(12) United States Patent
Vinogradov et al.

(10) Patent No.: US 8,742,755 B2
(45) Date of Patent: Jun. 3, 2014

(54) POSITIVE MAGNETIC RESONANCE IMAGING CONTRAST METHODS AND APPARATUS USING CHEMICAL EXCHANGE SATURATION TRANSFER

(75) Inventors: Elena Vinogradov, Boston, MA (US); Robert E. Lenkinski, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 732 days.

(21) Appl. No.: 12/936,711

(22) PCT Filed: Apr. 9, 2009

(86) PCT No.: PCT/US2009/002221
§ 371 (c)(1), (2), (4) Date: May 19, 2011

(87) PCT Pub. No.: WO2009/126289
PCT Pub. Date: Oct. 15, 2009

(65) Prior Publication Data
US 2011/0221440 A1    Sep. 15, 2011

Related U.S. Application Data

(60) Provisional application No. 61/123,534, filed on Apr. 9, 2008.

(51) Int. Cl.
*G01V 3/00* (2006.01)
(52) U.S. Cl.
USPC .......................................... 324/309; 324/307
(58) Field of Classification Search
USPC ........................... 324/300–322; 600/407–445
See application file for complete search history.

(56) References Cited

U.S. PATENT DOCUMENTS 6,850,793 B1 * 2/2005 Miyazaki et al. ............. 600/410
6,943,033 B2    9/2005 Van Zijl et al.

(Continued)

OTHER PUBLICATIONS

S. Aime, A. Barge, D. D. Castelli, F. Fedeli, A. Mortillaro, F. U. Nielsen and E. Terreno, "Paramagnetic lanthanide(III) complexes as pH-sensitive chemical exchange saturation transfer (CEST) contrast agents for MRI applications," *Magnetic Resonance in Medicine*, 2002, pp. 639-648, vol. 47.

(Continued)

*Primary Examiner* — Brij Shrivastav
(74) *Attorney, Agent, or Firm* — Wolf, Greenfield & Sacks, P.C.

(57) ABSTRACT

In one aspect, an apparatus for performing chemical exchange saturation transfer (CEST) magnetic resonance imaging on a region of an object being imaged is provided. The method comprises at least one coil capable of being operated to emit radio frequency (RF) signals, at least one detector capable of detecting nuclear magnetic resonance signals, and at least one controller to operate the at least one coil to provide at least one inversion sequence to the region to flip at least some spins in the region by a desired flip-angle, operate the at least one coil to provide at least one first pulse sequence at a first frequency offset from a peak resonant frequency of water by a first amount in a first direction to magnetize at least one exchange group in the region, operate the at least one coil to provide at least one second pulse sequence at a second frequency offset from the peak resonant frequency of water by the first amount in a second direction opposite the first direction, operate the at least one detector to measure a first signal emitted from the region as a result of providing the at least one first pulse sequence after a predetermined time interval after applying the first inversion sequence, and operate the at least one detector to measure a second signal emitted from the region as a result of providing the at least one second sequence at the predetermined time interval after applying the at least one inversion sequence, wherein the predetermined time interval is selected such that positive contrast is achieved with respect to the first signal relative to the second signal.

21 Claims, 7 Drawing Sheets

(56) References Cited

U.S. PATENT DOCUMENTS

| | | | |
|---|---|---|---|
| 8,131,338 B2* | 3/2012 | Kassai et al. | 600/410 |
| 2002/0188190 A1 | 12/2002 | Kassai et al. | |
| 2004/0061496 A1 | 4/2004 | Ookawa | |
| 2007/0134159 A1 | 6/2007 | Dixon et al. | |
| 2011/0221440 A1* | 9/2011 | Vinogradov et al. | 324/309 |
| 2012/0041299 A1* | 2/2012 | Kassai et al. | 600/413 |

OTHER PUBLICATIONS

A. P. Dagher, A. H. Alertas, P. Choyke and R. S. Balaban, "Imaging of urea using chemical exchange dependent saturation transfer at 1.5T," *Journal of Magnetic Resonance Imaging*, 2000, pp. 745-748, vol. 12.

V. Guivel-Scharen, T. Sinnwell, S. D. Wolff and R. S. Balaban, "Detection of Proton Chemical Exchange between Metabolites and Water in Biological Tissues," *J Magn Reson*, 1998, pp. 36-45, vol. 133.

K. Ward, A. H. Alertas and R. S. Balaban, "A New Class of Contrast Agents for MRI Based on Proton Chemical Exchange Dependent Saturation Transfer (CEST)," *J Magn Reson*, 2000, pp. 79-87, vol. 143.

K. Ward and R. S. Balaban, "Determination of pH using water protons and chemical exchange-dependent saturation transfer (CEST)," *Magnetic Resonance in Medicine*, 2000, pp. 799-802, vol. 44.

S. Zhang, P. Winter, K. Wu and A. D. Sherry, "A novel Europium(III)-based MRI contrast agent," *J Amer Chem Soc*, 2001, pp. 1517-1518, vol. 123.

S. Zhang, K. Wu and A. D. Sherry, "Unusually sharp dependence of water exchange rate versus Lanthanide ionic radii for a series of tetraamide complexes," *J Amer Chem Soc*, 2002, pp. 4226-4227, vol. 124.

International Search Report for International application No. PCT/US2009/002221 mailed Nov. 13, 2009.

* cited by examiner

POSITIVE MAGNETIC RESONANCE IMAGING CONTRAST METHODS AND APPARATUS USING CHEMICAL EXCHANGE SATURATION TRANSFER

CROSS-REFERENCE TO RELATED APPLICATION

This application is a national stage application under 35 U.S.C. §371 of International Application Ser. No. PCT/US2009/002221, filed Apr. 9, 2009, entitled "POSITIVE MAGNETIC RESONANCE IMAGING CONTRAST METHODS AND APPARATUS USING CHEMICAL EXCHANGE SATURATION TRANSFER," which claims the benefit under 35 U.S.C. §119(e) of U.S. Provisional Application 61/123,534, filed Apr. 9, 2008, entitled "POSITIVE MAGNETIC RESONANCE IMAGING CONTRAST METHODS AND APPARATUS USING CHEMICAL EXCHANGE SATURATION TRANSFER," which is incorporated herein in its entirety.

TECHNICAL FIELD

The present disclosure relates to magnetic resonance imaging (MRI) and, more particularly, to chemical exchange saturation transfer (CEST) and paramagnetic chemical saturation transfer (PARACEST) techniques.

BACKGROUND

Chemical exchange processes in tissue may be visualized using magnetic resonance imaging (MRI) employing a chemical exchange saturation transfer (CEST) methodology. CEST imaging exploits the ability of nuclear magnetic resonance (NMR) to resolve different signals arising from protons of different molecules. CEST techniques operate by detecting the exchange mediated saturation transfer between bound and bulk protons by utilizing exchanging groups (e.g., —OH and —NH) of small organic molecules. In particular, the transfer of magnetization from the exchange group and/or contrast agent attenuates the bulk water signal. This attenuation of the bulk water signal can be measured and used to provide contrast in MRI.

Figure 1A:
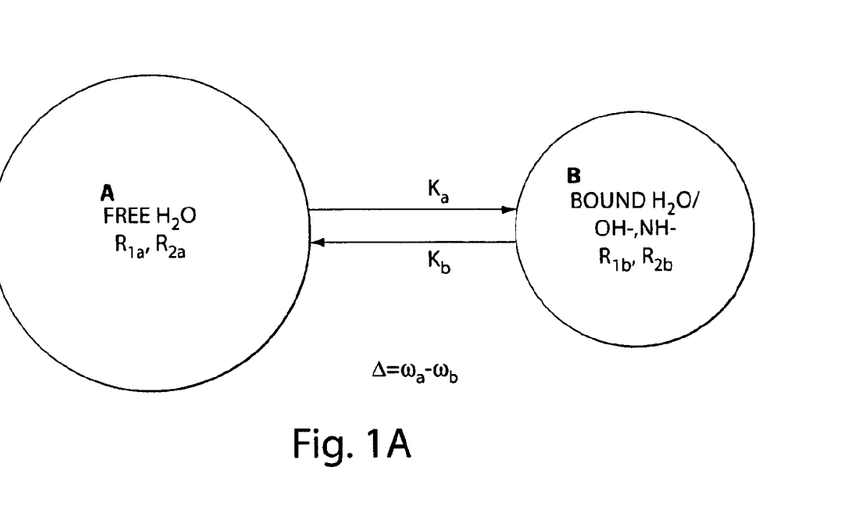
FIG. 1A illustrates the exchange kinetics $k_a$ and $k_b$ between the bulk (A) and bound (B) protons.
Figure 1B:
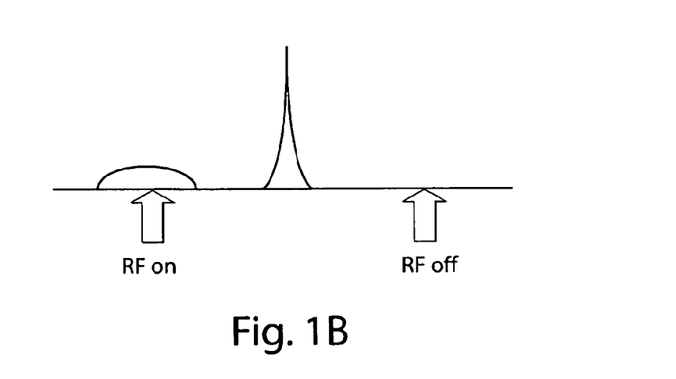
FIG. 1B illustrates an RF ON frequency and an RF OFF frequency relative to the peak resonant frequency of water.

FIG. 1A illustrates the principle behind CEST techniques. In particular, FIG. 1A illustrates exchange kinetics $k_a$ and $k_b$ between the bulk protons (A) and the bound protons (B). When RF irradiation is applied at a frequency of the chemical shift of an exchanging group (e.g., —OH or —NH) as shown in FIG. 1B (RF ON), the RF saturation is transferred to the surrounding bulk water molecules resulting in a relatively small yet detectable decrease in the strong water signal (i.e., negative contrast is generated). CEST imaging is relatively sensitive to the environment of the exchanging group and/or contrast agent and has found a number of applications such as the detection of pH, metabolite levels, protein depletion, etc.

CEST techniques may be supplemented or complemented by using paramagnetic complexes as MRI contrast agents. Such techniques are referred to as PARACEST. For example, exogenous paramagnetic lanthanide complexes exhibit slow exchange kinetics between an inner coordination site and bulk water and show large chemical shifts for lanthanide-bound water molecules. Similar to the CEST effect, PARACEST contrast is generated via application of a saturating RF sequence at a frequency corresponding to the chemical shift of the water protons bound to the paramagnetic complex. Utilization of PARACEST may provide several advantages over CEST, for example, PARACEST techniques may provide increased sensitivity enabling detection of the paramagnetic contrast agents in the microMolar concentration range.

SUMMARY

Some embodiments include a computer readable medium having processor-executable instructions stored thereon, the processor-executable instructions, when executed by at least one processor, performing a method of performing chemical exchange saturation transfer (CEST) magnetic resonance imaging on a region of an object, the method comprising providing at least one inversion sequence to the region to flip at least some spins in the region by a desired flip-angle, providing at least one first pulse sequence at a first frequency offset from a peak resonant frequency of water by a first amount in a first direction to magnetize at least one exchange group in the region, providing at least one second pulse sequence at a second frequency offset from the peak resonant frequency of water by the first amount in a second direction opposite the first direction, detecting a first signal emitted from the region as a result of providing the at least one first pulse sequence after a predetermined time interval after applying the at least one inversion sequence, and detecting a second signal emitted from the region as a result of providing the at least one second pulse sequence at the predetermined time interval after applying the at least one inversion sequence, wherein the predetermined time interval is selected such that positive contrast is achieved with respect to the first signal relative to the second signal.

Some embodiments include a method of performing chemical exchange saturation transfer (CEST) magnetic resonance imaging on a region of an object being imaged, the method comprising operating at least one coil to provide at least one inversion sequence to the region to flip at least some spins in the region by a desired flip-angle, operating the at least one coil to provide at least one first pulse sequence at a first frequency offset from a peak resonant frequency of water by a first amount in a first direction to magnetize at least one exchange group in the region, operating the at least one coil to provide at least one second pulse sequence at a second frequency offset from the peak resonant frequency of water by the first amount in a second direction opposite the first direction, operating at least one detector to measure a first signal emitted from the region as a result of providing the at least one first pulse sequence after a predetermined time interval after applying the at least one inversion sequence, operating at least one detector to measure a second signal emitted from the region as a result of providing the at least one second sequence at the predetermined time interval after applying the at least one inversion sequence, wherein the predetermined time interval is selected such that positive contrast is achieved with respect to the first signal relative to the second signal.

Some embodiments include an apparatus for performing chemical exchange saturation transfer (CEST) magnetic resonance imaging on a region of an object being imaged, the method comprising at least one coil capable of being operated to emit radio frequency (RF) signals, at least one detector capable of detecting nuclear magnetic resonance signals, and at least one controller to operate the at least one coil to provide at least one inversion sequence to the region to flip at least some spins in the region by a desired flip-angle, operate the at least one coil to provide at least one first pulse sequence at a first frequency offset from a peak resonant frequency of water by a first amount in a first direction to magnetize at least one exchange group in the region, operate the at least one coil to provide at least one second pulse sequence at a second frequency offset from the peak resonant frequency of water by the first amount in a second direction opposite the first direction, operate the at least one detector to measure a first signal emitted from the region as a result of providing the at least one first pulse sequence after a predetermined time interval after applying the first inversion sequence, and operate the at least one detector to measure a second signal emitted from the region as a result of providing the at least one second sequence at the predetermined time interval after applying the at least one inversion sequence, wherein the predetermined time interval is selected such that positive contrast is achieved with respect to the first signal relative to the second signal.

DETAILED DESCRIPTION

As discussed above, CEST/PARACEST techniques can be used to obtain contrast in MRI imaging. However, a significant drawback of conventional CEST/PARACEST methodologies involve the fact that the contrast in conventional CEST/PARACEST techniques is negative, i.e., such conventional techniques are aimed at detecting a decrease in an NMR signal. Specifically, conventional CEST/PARACEST techniques seek to measure the decrease in the bulk water signal due to saturation transfer. Thus, negative contrast is typically characterized by detection of relatively small changes to a relatively large overall signal. Accordingly, CEST/PARACEST techniques often exhibit a relatively low signal-to-noise ratio (SNR).

Applicant has recognized and appreciated that the sensitivity of conventional CEST/PARACEST methods may be improved by modifying various parameters of the standard radio-frequency (RF) pulse sequence typically employed in CEST/PARACEST imaging. According to some embodiments, the RF sequences applied to a region being imaged are provided so as to provide positive contrast in a CEST/PARACEST imaging procedure. In the presence of RF irradiation applied at the on-resonance of the exchanging pool (bound protons), the apparent relaxation time of water (bulk protons) decreases. Applicant has appreciated that this change in relaxation, combined with an inversion sequence, may be used to create a positive CEST/PARACEST contrast.

By modifying the RF pulse sequence according to various embodiments, an intensity increase on a low background signal may be detected, resulting in improved and positive contrast. That is, the CEST/PARACEST signal can be converted from a negative contrast to a positive contrast, as discussed in further detail below.

In some embodiments, the RF sequence used in a CEST/PARACEST imaging procedure includes an inversion sequence provided before an RF saturation sequence to invert and/or otherwise condition the spins in an imaging region. When an RF sequence is applied at a frequency offset $\Delta$ (relative to the resonant frequency of water) corresponding to the chemical shift of an exchanging group and/or contrast agent, the apparent relaxation time ($T_1$ or $R_{1(app)}$) of the free water increases relative to the $T_1$ measured when the RF sequence is applied at a frequency applied at the same frequency offset but applied to the opposite side of the peak resonant frequency of water, where no exchanging groups are present (i.e., applied at an offset frequency $-\Delta$). The magnitude of the frequency offset $\Delta$ will depend on the type of exchanging group and/or contrast agent. In combination with an inversion sequence, this change in apparent relaxation time may be exploited to appropriately time signal detection during an interval in which positive contrast is present, as discussed in further detail below.

In some embodiments, the timing of RF pulse sequences are adjusted to create a relatively large positive magnetization when an RF pulse sequence is applied at the on-resonance frequency of the exchanging group (i.e., at RF ON corresponding to the frequency offset $\Delta$) and an approximately null or relatively small positive magnetization when an RF pulse sequence is applied at off-resonance (i.e., RF OFF corresponding to the frequency offset $-\Delta$). In combination with an inversion sequence, a positive signal over a relatively low intensity background may be generated. The suppression of the background signal may result in a higher sensitivity detection scheme relative to conventional approaches. Moreover, achieving a null or relatively small background signal may increase the SNR and may suppress motion effects.

Following below are more detailed descriptions of various concepts related to, and embodiments of, methods and apparatus according to the present disclosure for generating positive MRI contrast using modified CEST/PARACEST methods. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 2A:
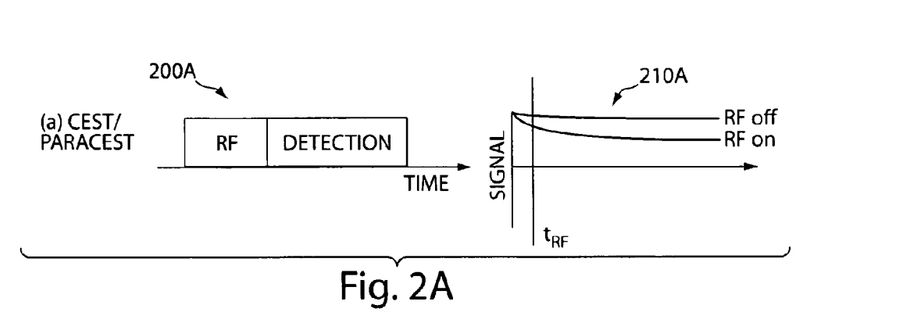
FIG. 2A illustrates a conventional CEST imaging sequence and the resulting negative contrast NMR signals.

A conventional RF sequence used for CEST/PARACEST imaging is illustrated in FIG. 2A as sequence 200A, which is comprised of an RF saturation period wherein a saturation pulse sequence is applied, followed by a detection period during which signals emitted from the region being imaged are measured. As described above, in CEST/PARACEST imaging, RF irradiation may be applied at the frequency of the chemical shift $\Delta=\omega_a-\omega_b$ of the exchanging group (e.g., —OH or —NH), where $\omega_a$ is the frequency of the bulk water peak, and $\omega_b$ is the frequency of the exchanging group as shown in FIG. 1B as RF ON. In this situation, the RF saturation is transferred to the surrounding bulk water molecules resulting in a relatively small yet detectable decrease in the strong water signal (i.e., negative contrast is generated) as shown by the plot 210A of RF ON and RF OFF signals resulting from the conventional RF sequence.

As shown, the signal measured as a result of RF irradiation being applied at a frequency on the opposite side of the bulk water peak (i.e., at $-\Delta=\omega_b-\omega_a$ or RF OFF) is larger than the signal obtained using the RF sequence applied at the chemical shift of the exchanging group (RF ON), thus resulting in negative contrast (i.e., the signal decrease corresponds to the imaging or contrast information). The reason for this is that the lack of detected bound contrast agent at the RF OFF frequency leads to a negligible reduction in the strong water signal. At a time $t_{RF}$ (i.e., at the beginning of the "detection" period), a reduction in the signal for the RF ON condition compared to the RF OFF condition reflects the negative contrast generated by the conventional CEST/PARACEST scheme.

In some embodiments, the conventional CEST/PARACEST scheme is modified so that a positive MRI contrast is generated. In one implementation, this may be achieved by using a modified RF imaging sequence such as that shown schematically as 200B in FIG. 2B. In the illustrative example of FIG. 2B, the modified RF pulse sequence begins with an inversion sequence, followed by a saturation period wherein a saturation pulse sequence is applied. After a predetermined time interval subsequent to the application of the inversion sequence (labeled as $t_{RF}$), the signal resulting from applying the RF sequence (RF ON) at the chemical shift of the exchanging group will be positive and greater than the signal resulting from applying an RF sequence at the frequency offset on the opposite side of the peak water frequency, thus providing positive contrast.

Figure 2B:
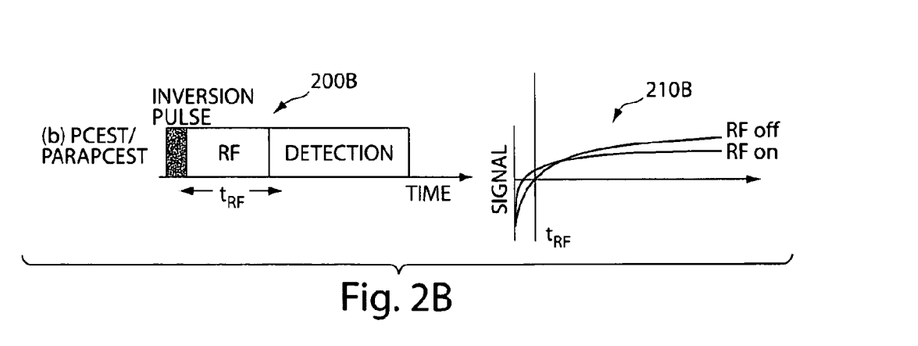
FIG. 2B illustrates a CEST imaging sequence and the resulting positive contrast NMR signals, in accordance with some embodiments of the present invention.

As with conventional CEST/PARACEST imaging, when the saturation sequence is applied at a frequency of the chemical shift of an exchanging site (RF ON), the apparent free water relaxation time (T1) decreases, i.e., the magnetization reaches the steady-state faster than if the RF is applied at the same frequency offset at the opposite side of the water peak (RF OFF). In some embodiments, the inversion sequence produces approximately a 180° flip in the proton spins, so that the detected water signal begins at a negative value and increases as illustrated by the signals shown in 210B, as contrasted to the large positive value followed by a signal decrease observed using conventional CEST/PARACEST imaging as shown in 210A.

The timing of the RF pulse may be adjusted to be somewhat longer than the time corresponding to the null signal in the RF OFF condition. The intensity of the RF pulse may be adjusted so that when RF is applied in the on-resonance condition (RF ON), the water magnetization reaches a positive value higher than when the RF is applied off-resonance (RF OFF). Thus, very little signal may be generated in the RF OFF condition, and a much larger signal may be generated in the RF ON condition at the time the signals are measured. Thus, at a time $t_{RF}$ corresponding to the beginning of the detection period, a positive contrast may be observed, since the signal in the RF ON condition is larger than the signal in the RF OFF condition (which may be close to null). That is, $t_{RF}$ may be chosen so that during detection, the background signal is substantially zero and the signal resulting from the contrast agent is positive, thus resulting in a positive contrast.

Positive contrast for CEST/PARACEST imaging may be achieved by modifying one or more selected RF pulse sequence parameters. By beginning the RF sequence with an inversion sequence, the recovery signal in the RF OFF condition may at some time point $T_{null}$ have a value very close to zero, thereby enabling background suppression of the measured signal. Additionally, a suitable RF intensity may be determined for various CEST or PARACEST contrast agents to accelerate the apparent relaxation under saturation of the exchanging pool, resulting in an observed positive contrast, as discussed in further detail below.

Figure 3:
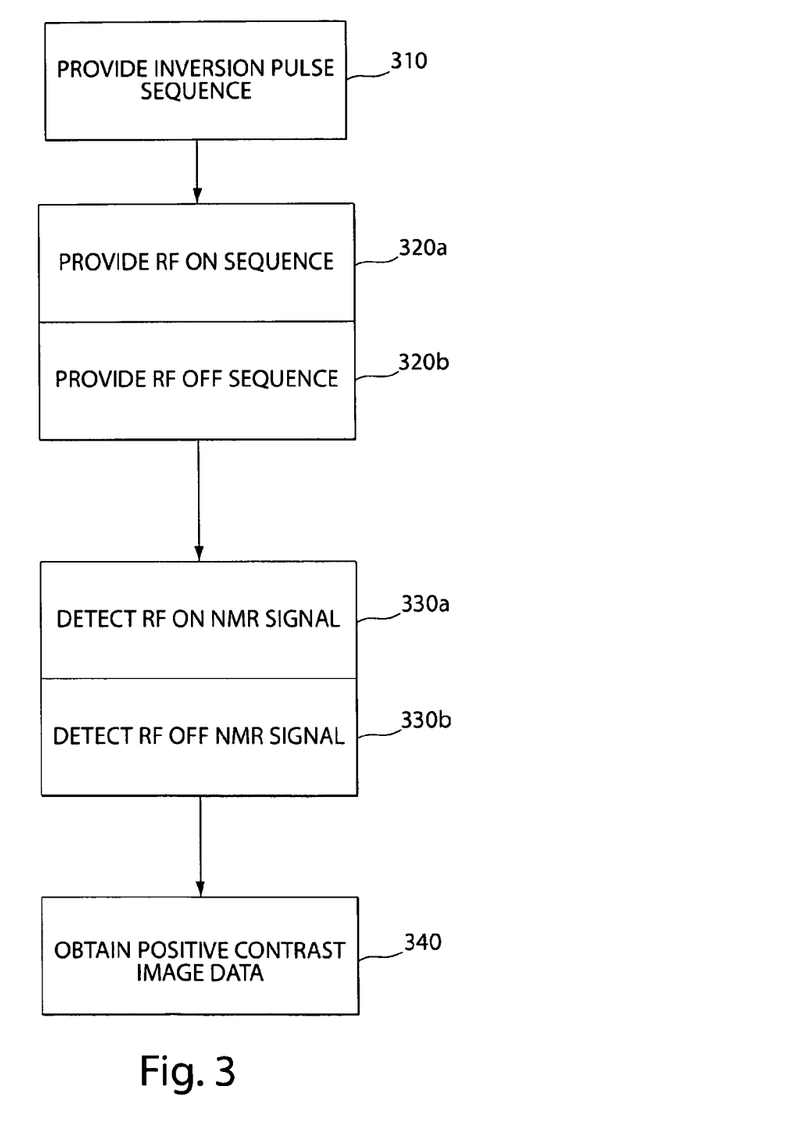
FIG. 3 illustrates a method of performing positive contrast CEST imaging, in accordance with some embodiments of the present invention.

FIG. 3 illustrates a method of performing positive contrast CEST imaging, in accordance with some embodiments of the present invention. In act 310, at least one inversion sequence is provided to the region being imaged to flip spins in the region being imaged. As discussed above, the inversion sequence conditions the spins such that NMR signals emitted from the region after one or more imaging sequences are applied are inverted and begin negative and increase over a subsequent time interval. The inversion sequence may be one or more pulses adapted to achieve the desired flip-angle to condition the region for imaging. In some embodiments, a flip angle of approximately 180 degrees is used. However, other flip angles that condition the region such that negative NMR signals are initially emitted after one or more imaging sequences are applied may be used, as the aspects of the invention are not limited in this respect.

In act 320a, a first pulse sequence may be applied to magnetize the region. The first pulse sequence may be applied at a frequency corresponding to an exchange group and/or contrast agent in the region. For example, the frequency may correspond to the chemical shift of the exchange group and be offset from the peak water signal in a first direction. Any pulse sequence capable of causing a chemical exchange saturation effect may be used, as the aspects of the invention are not limited in this respect. In act 320b, a second pulse sequence may be applied at a frequency offset from the peak water frequency by the same amount as the frequency of the first pulse sequence but in the other direction (i.e., on the other side of the peak resonant frequency of water). Because there may be no exchanging group and/or contrast agent responding at the frequency of the second pulse sequence, the peak water signal will experience little or no attenuation.

In act 330a, a first signal is detected by measuring NMR signals emitted from the region as a result of applying the first pulse sequence. As a result of the at least one inversion sequence, the first signal may begin negative and increase in magnitude as a function of time. According to some embodiments, the first signal is measured after a predetermined time interval subsequent to the application of the at least one inversion sequence such that the first signal has increased from a negative signal and takes on positive values. In act 330b, a second signal resulting from applying the second pulse sequence may be measured after the predetermined time interval. The second signal may be used as a reference to determine the contrast in an image of the region. According to some embodiments, the predetermined time interval is selected such that the second signal is measured approximately when the second signal transitions from a negative signal to a positive signal. That is, the timing for detecting the second signal may be chosen so that the second signal is null or near zero. Due to the change in the apparent relaxation times, the first signal will be larger than the second during this transition, thus achieving positive contrast. As a result, the contrast may be a relatively large signal (i.e., the first signal) over a relatively small (e.g., a substantially suppressed second signal) background signal. Accordingly, increased sensitivity, higher signal-to-noise ratio and/or increased insensitivity to motion may be achieved.

It should be appreciated that applying the first and second pulse sequences and acquiring the first and second signals may be performed in parallel (e.g., simultaneously) or in series, wherein at least one inversion sequence would be applied prior to each serially applied pulse sequence and serially acquired resulting NMR signal. That is, in embodiments wherein NMR signals are obtained separately for the RF ON and RF OFF frequency, the at least one inversion sequence, the RF sequence and the signal detection may be repeated for the RF ON and RF OFF condition using the same delay in detecting the emitted NMR signals. In embodiments wherein imaging is performed in parallel, the at least one inversion sequence may be used to condition the spins for both the RF ON and RF OFF sequences that are applied at the same time. Other combinations of sequences that achieve positive contrast may be used, as the aspects of the invention are not limited in this respect.

Applicant has also recognized that contrast effects may also depend on the concentration of the contrast unit in solution. Although the absolute intensity change may in some cases be smaller for the modified CEST/PARACEST scheme compared to the standard CEST/PARACEST scheme, the modified scheme benefits from the signal suppression observed when the RF is OFF.

Figure 4A:
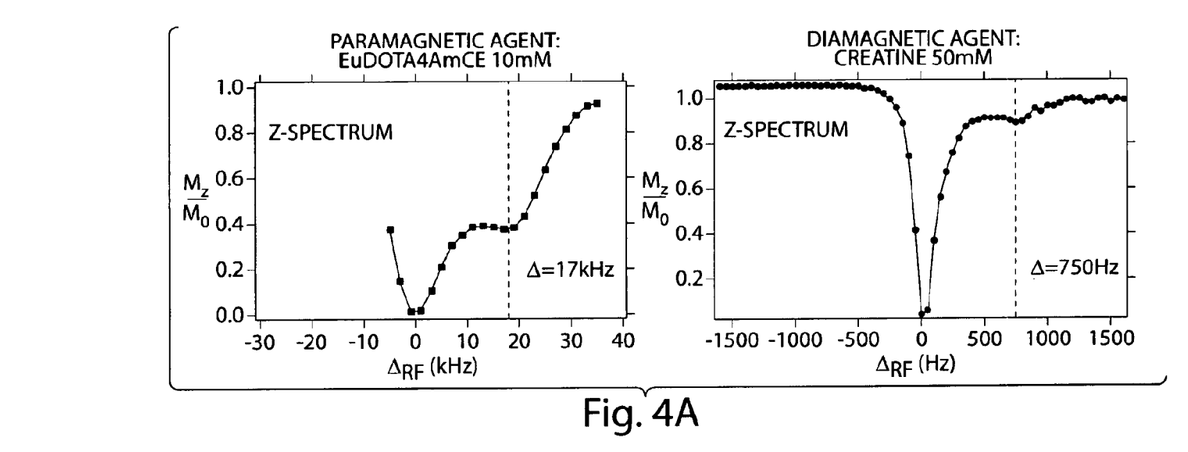
FIG. 4 illustrates the measured Z-spectrum (frequency-dependent water saturation spectrum) for a paramagnetic contrast agent 10 mM EuDOTA4AmCE that may be used in PARACEST imaging, and a diamagnetic contrast agent 50 mM Creatine that may be used in CEST imaging, and the apparent relaxation times of same.
Figure 4B:
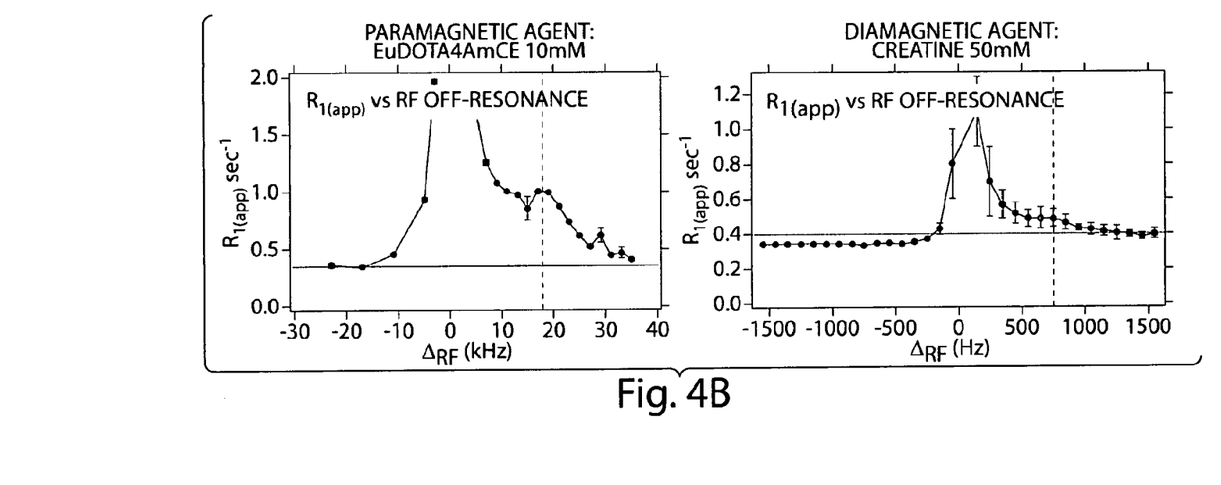

Applicant has appreciated that in the presence of off-resonance irradiation and exchange, the apparent relaxation rate ($R_{1(app)}$) of the free water depends on the RF off-resonance and intensity as shown in FIG. 4. FIG. 4 in the plots labeled a) illustrate the measured Z-spectrum (frequency-dependent water saturation spectrum) for a paramagnetic contrast agent 10 mM EuDOTA4AmCE that may be used in PARACEST imaging, and a diamagnetic contrast agent 50 mM Creatine that may be used in CEST imaging. Each contrast agent (e.g., EuDOTA4AmCE, Creatine, etc.) has a characteristic value $\Delta$ which is the frequency distance between the free water peak and the on-resonance frequency of the contrast agent. In the illustrative example of FIG. 4, in the plots labeled a), 10 mM EuDOTA4AmCE has a $\Delta$ of 17 kHz, whereas 50 mM Creatine has a $\Delta$ of 750 Hz.

To determine the relationship between $R_{1(app)}$ and RF off-resonance ($\Delta_{RF}$), different values of $\Delta_{RF}$ may be employed, and the resulting $R_{1(app)}$ may be determined as shown in FIG. 4 in the plots labeled b). As illustrated in FIG. 4, the plot of $R_{1(app)}$ vs. $\Delta_{RF}$ agrees well with the Z-spectra shown in FIG. 4, and $R_{1(app)}$ shows a local maximum when $\Delta_{RF}$ equals the characteristic value $\Delta$ for each contrast agent.

Applicant has further recognized that higher exchange rates, such as those observed for paramagnetic compounds, may require higher RF power to induce observable effects. Thus, similar to CEST imaging using organic molecules, PARACEST imaging using paramagnetic compounds may result in larger changes in $R_{1(app)}$ as illustrated in FIG. 4. However, an increased RF intensity may be required to observe this result. To study the effect of RF intensity on $R_{1(app)}$ for the two contrast agents shown in FIG. 4, measurements of $R_{1(app)}$ may be made when RF is applied at the on-resonance frequency (RF ON) and at the frequency on the opposite side of the water peak (RF OFF) while RF intensity is varied, as shown in FIG. 5.

Figure 5:
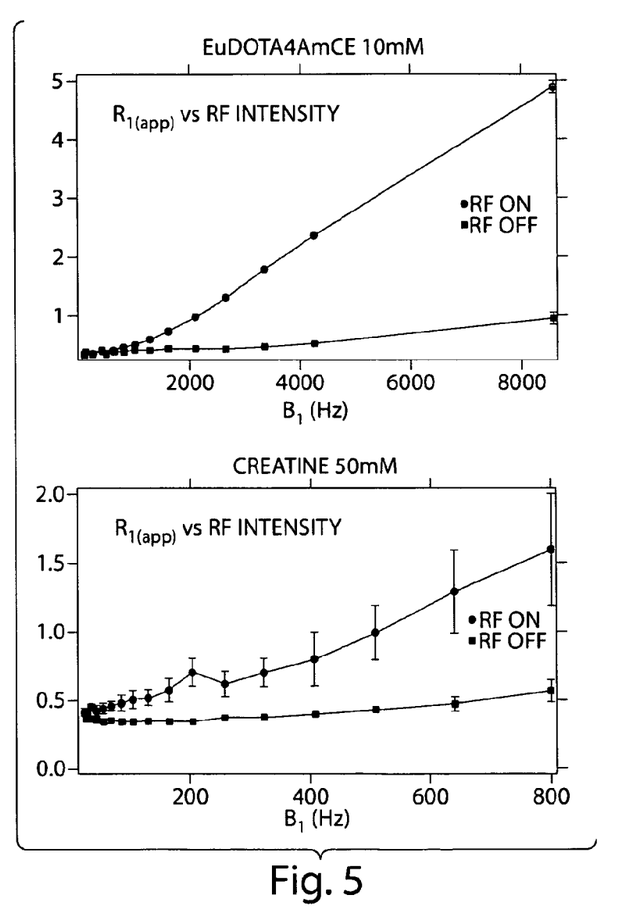
FIG. 5 illustrates apparent relaxation time versus RF intensity for EuDOTA4AmCE and Creatine.

As illustrated in FIG. 5, when RF is applied on-resonance with the exchanging pool (RF ON), the increase in RF intensity ($B_1$) results in an increase in the apparent relaxation rate $R_{1(app)}$. Applicant has appreciated that spill over effects may reduce the difference in signals detected in the RF ON vs. RF OFF conditions. Thus, by also measuring $R_{1(app)}$ in the RF OFF condition, it was confirmed that spill-over effects cause only a slight increase in $R_{1(app)}$, while saturation exchange results in greater effects on $R_{1(app)}$.

Figure 6A:
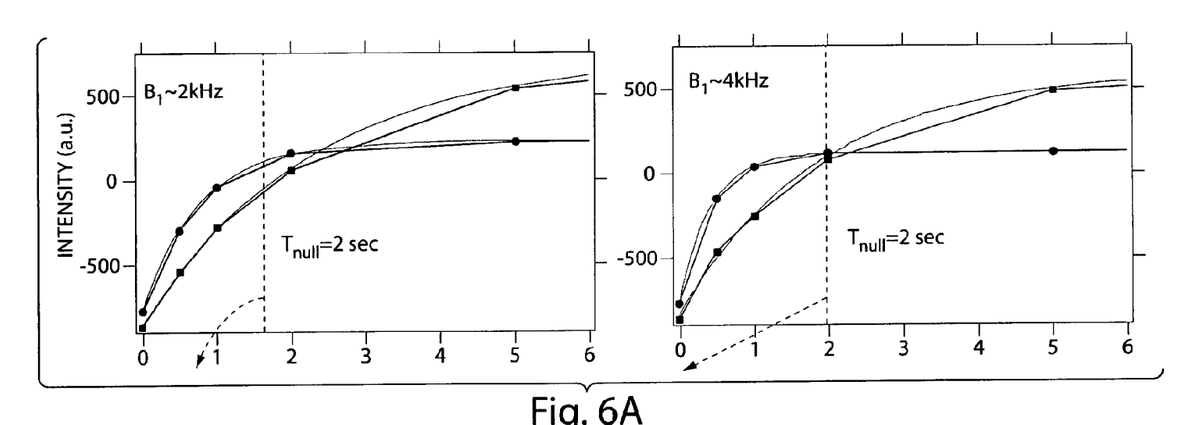
FIG. 6 illustrates the recovery curves for the Eu contrast agent for two different RF intensities, 2 kHz and 4 kHz.
Figure 6B:
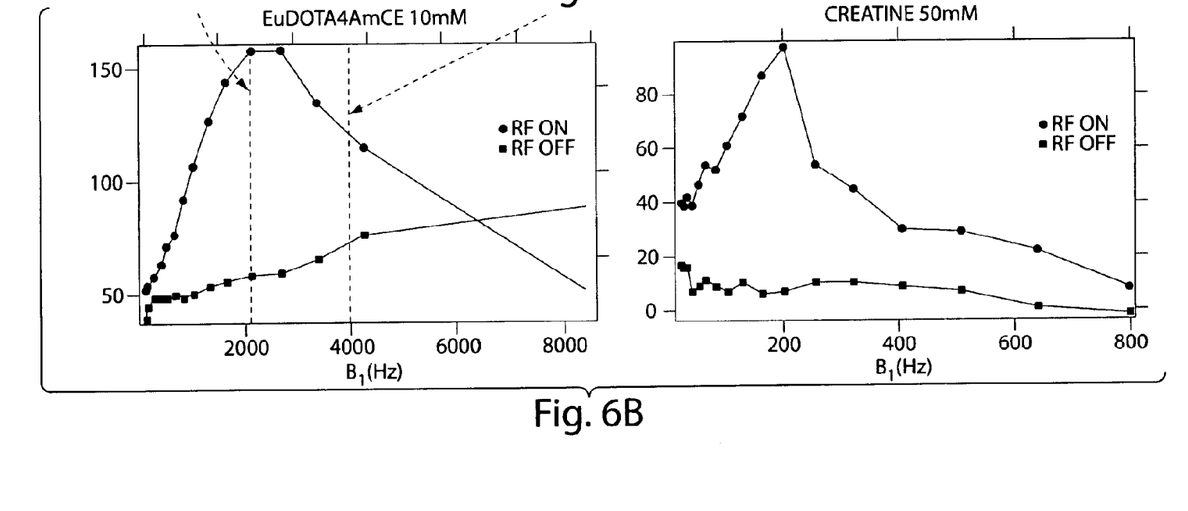

Applicant has also recognized that acceleration of relaxation (i.e., increasing $R_{1(app)}$) may not always result in the desired positive contrast effect. For example, if the steady-state magnetization is lower than at equilibrium, and if the RF intensity is too high, the intensity in the RF ON condition may never be higher than in the RF OFF condition. An example of this situation is illustrated in FIG. 5a (right) for the contrast agent EuDOTA4AmCE. FIG. 6 shows the recovery curves for the Eu contrast agent for two different RF intensities (left: 2 kHz, right: 4 kHz).

Thus, it may be of benefit to select a suitable RF intensity $B_1$ for each contrast agent used in the CEST/PARACEST imaging, such that $B_1$ will be large enough to produce greater values of $R_{1(app)}$, but small enough so that the steady state magnetization is not lower than at equilibrium, as shown in FIG. 6 (right). To determine a suitable value of $B_1$, a value $T_{null}$ may be determined from the plots in FIG. 6, when the signal in the RF OFF condition is close to zero (or slightly positive). In the illustrative example of FIG. 6, the value of $T_{null}$ is approximately 2 seconds for each of the contrast agents. FIG. 6 illustrates the intensity at $T_{null}$, versus RF intensity for the RF ON and RF OFF conditions. To determine a suitable value of $B_1$, RF intensity may be adjusted to determine which values of $B_1$ provide the largest positive contrast signal in the RF ON condition. As illustrated in FIG. 6, the largest signal in the RF ON condition is dependent on the exchange rate of the contrast agent. For example, the paramagnetic Eu contrast agent, which has a higher exchange rate, has suitable $B_1$ values in the range between approximately 2000 and 3000 Hz, whereas the diamagnetic Creatine contrast agent has suitable $B_1$ values around 200 Hz. Thus, similar to the conventional CEST/PARACEST scheme, the modified CEST/PARACEST scheme may employ suitable RF intensities that are proportional to the exchange rate of the contrast agent being used.

Figure 7:
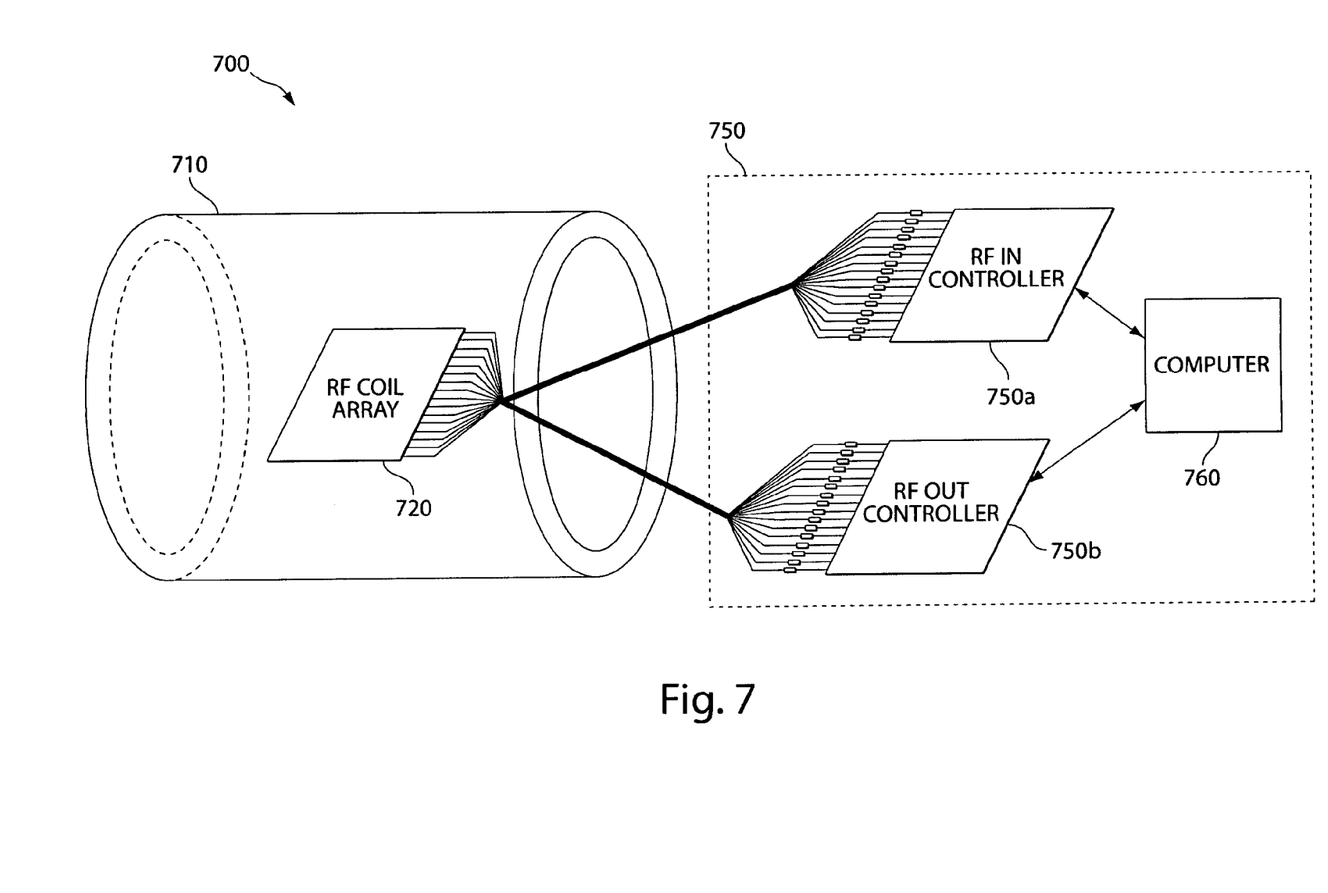
FIG. 7 illustrates an imaging apparatus suitable for performing methods described herein.

FIG. 7 illustrates an MR scanner configurable to obtain MR images, and more particularly, to obtain NMR data using various methods described in the foregoing. Specifically, scanner 700 may be used to implement the various CEST/PARACEST techniques described herein. Scanner 700 includes a magnet 710 capable of producing a magnetic field of desired field strength to align spin properties of molecules of a subject positioned in the interior of the magnet. Magnet 710 may be any of various MR magnets conventionally used in clinical MRI (e.g., approximately 1.5-3.0 T) or may be a high-field magnet (e.g., 3-7 T or higher) and may produce a uniform or gradient magnetic field. Magnet 710 may be of any shape, size and strength and is shown as substantially circular in shape for the purposes of schematic illustration only. For example, magnet 710 may be any magnet or collection of magnets used in clinical or research MRI scanners.

Scanner 700 includes an array 720 of one or more RF coils arranged proximate the magnet and adapted to perform at least some MR operations. In particular, the RF coil(s) in coil array 720 may be adapted to provide RF pulse sequences and to detect NMR signals emitted from an object being imaged. RF coil array may include a single RF coil, or may include multiple RF coils in any configuration, as the aspects of the invention are not limited in this respect. For example, RF coil array 720 may be an $L(M_t,N_r)$ array where L is the number of coils in the array and $M_t$ and $N_r$ are the number of independent transmit and receive channels, respectively. As stated above, L may indicate a single or multiple coil array.

Scanner 700 may further include controller 750 coupled to coil array 720. Controller 750 comprises an RF IN controller 750a and an RF OUT controller 750b. RF IN controller 750a is adapted to provide and control RF power to the RF coil array 720. In particular, RF IN controller 750a is configured to provide RF power across the M independent transmit channels to respective coils in the array. Similarly, RF OUT controller 750b is adapted to measure one or more properties of the RF coils over the N independent reception channels in the array. Controller 750 may be a network analyzer or a custom made controller, signal generator and/or other components adapted to transmit RF power to, and obtain measurements from, coil array 720.

Controller 750 may include a computer 760, either connected to RF IN controller 750a, RF OUT controller 750b, or both. Computer 760 may include one or more programs configured to control various aspects of the RF pulse sequences initiated by RF IN controller 750a and ultimately provided to an object or region being imaged by coil array 720. For example, computer 760 may include one or more programs that define the timing, amplitude, phase and any other signal characteristics of RF pulse sequences to be provided by coil array 720. In particular, computer 760 may instruct RF IN controller 750a to excite the coil array according to any of the various RF pulse sequences described in the foregoing.

Computer 760 may include one or more programs configured to control the synchronization of controller 750 and/or control the sequencing of various operations performed by scanner 700. For example, computer 760 may be configured to synchronize RF IN controller 750a and RF OUT controller 750b to provide RF pulse sequences and detect emitted NMR signals, for example, according to various timing sequences. For example, computer 760 may be configured to operate the scanner 700 to perform the various CEST/PARACEST timing sequences to achieve positive contrast imaging. Computer 760 may be configured to operate scanner 700 to transmit and receive signals according to any desired schedule, as the aspects of the invention are not limited in this respect. Thus, controller 750 may be configured to deliver any of the various pulse sequences described in the foregoing and/or other appropriate or desired pulse sequences and/or timing and imaging schemes.

Having thus described one or more illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code. In this respect, it should be appreciated that some embodiments are directed to a computer-readable medium or multiple computer-readable media (e.g., a computer memory, one or more floppy disks, compact disks, optical disks, magnetic tapes, etc.) encoded with one or more programs that, when executed, on one or more computers or other processors, perform methods that implement the various embodiments described herein. The computer-readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that, when executed, perform methods of the present invention need not reside on a single computer or processor, but may be distributed in a modular fashion amongst a number of different computers or processors to implement various aspects of the present invention.

It should be appreciated that various aspects of the present invention may be may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. Various aspects of the present invention may be implemented in connection with any type MR imaging equipment of any configuration. No limitations are placed on scanner implementation. Accordingly, the foregoing description and drawings are by way of example only. Moreover, various aspects of the present invention may be practiced with any number of coil types and arrangements. For example, generally planar coils, birdcage coils, surface and volume coils may be used alone or in any combination with the any of the various imaging techniques described herein. Likewise, various aspects may be practiced with any type of detector such as coils, phase sensitive detectors and/or any other type or combination of detectors.

In addition, various aspects of the invention described in one embodiment may be used in combination with other embodiments and is not limited by the arrangements and combinations of features specifically described herein. Various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A computer readable medium having processor-executable instructions stored thereon, the processor-executable instructions, when executed by at least one processor, performing a method of performing chemical exchange saturation transfer (CEST) magnetic resonance imaging on a region of an object, the method comprising:
providing at least one inversion sequence to the region to flip at least some spins in the region by a desired flip-angle;
providing at least one first pulse sequence at a first frequency offset from a peak resonant frequency of water by a first amount in a first direction to magnetize at least one exchange group in the region;
providing at least one second pulse sequence at a second frequency offset from the peak resonant frequency of water by the first amount in a second direction opposite the first direction;
detecting a first signal emitted from the region as a result of providing the at least one first pulse sequence after a predetermined time interval after applying the at least one inversion sequence; and
detecting a second signal emitted from the region as a result of providing the at least one second pulse sequence at the predetermined time interval after applying the at least one inversion sequence, wherein the predetermined time interval is selected such that positive contrast is achieved with respect to the first signal relative to the second signal.

2. The computer readable medium of claim 1, wherein at least one inversion sequence is adapted to condition the spins such that the first signal and the second signal begin negative and increase during the predetermined time interval.

3. The computer readable medium of claim 2, wherein at least one inversion sequence is provided to flip at least some of the spins in the region by approximately 180 degrees.

4. The computer readable medium of claim 2, wherein the predetermined time interval is selected such that the first signal is detected when it is positive.

5. The computer readable medium of claim 2, wherein the predetermined time interval is selected such that the second signal is detected when the second signal is approximately zero.

6. The computer readable medium of claim 1, wherein the exchange group includes at least one contrast agent.

7. The computer readable medium of claim 1, wherein the exchange group includes at least one paramagnetic contrast agent.

8. A method of performing chemical exchange saturation transfer (CEST) magnetic resonance imaging on a region of an object being imaged, the method comprising:
operating at least one coil to provide at least one inversion sequence to the region to flip at least some spins in the region by a desired flip-angle;
operating the at least one coil to provide at least one first pulse sequence at a first frequency offset from a peak resonant frequency of water by a first amount in a first direction to magnetize at least one exchange group in the region;
operating the at least one coil to provide at least one second pulse sequence at a second frequency offset from the peak resonant frequency of water by the first amount in a second direction opposite the first direction;
operating at least one detector to measure a first signal emitted from the region as a result of providing the at least one first pulse sequence after a predetermined time interval after applying the at least one inversion sequence;
operating at least one detector to measure a second signal emitted from the region as a result of providing the at least one second sequence at the predetermined time interval after applying the at least one inversion sequence, wherein the predetermined time interval is selected such that positive contrast is achieved with respect to the first signal relative to the second signal.

9. The method of claim 8, wherein at least one inversion sequence is adapted to condition the spins such that the first signal and the second signal begin negative and increase during the predetermined time interval.

10. The method of claim 9, wherein at least one inversion sequence is provided to flip at least some of the spins in the region by approximately 180 degrees.

11. The method of claim 9, wherein the predetermined time interval is selected such that the first signal is measured when the first signal is positive.

12. The method of claim 9, wherein the predetermined time interval is selected such that the second signal is measured substantially when the second signal is approximately zero.

13. The method of claim 8, wherein the exchange group includes at least one contrast agent.

14. The method of claim 8, wherein the exchange group includes at least one paramagnetic contrast agent.

15. An apparatus for performing chemical exchange saturation transfer (CEST) magnetic resonance imaging on a region of an object being imaged, the method comprising:
at least one coil capable of being operated to emit radio frequency (RF) signals;
at least one detector capable of detecting nuclear magnetic resonance signals; and
at least one controller to operate the at least one coil to provide at least one inversion sequence to the region to flip at least some spins in the region by a desired flip-angle, operate the at least one coil to provide at least one first pulse sequence at a first frequency offset from a peak resonant frequency of water by a first amount in a first direction to magnetize at least one exchange group in the region, operate the at least one coil to provide at least one second pulse sequence at a second frequency offset from the peak resonant frequency of water by the first amount in a second direction opposite the first direction, operate the at least one detector to measure a first signal emitted from the region as a result of providing the at least one first pulse sequence after a predetermined time interval after applying the first inversion sequence, and operate the at least one detector to measure a second signal emitted from the region as a result of providing the at least one second sequence at the predetermined time interval after applying the at least one inversion sequence, wherein the predetermined time interval is selected such that positive contrast is achieved with respect to the first signal relative to the second signal.

16. The apparatus of claim 15, wherein at least one inversion sequence is adapted to condition the spins such that the first signal and the second signal begin negative and increase during the predetermined time interval.

17. The apparatus of claim 16, wherein at least one inversion sequence is provided to flip at least some of the spins in the region by approximately 180 degrees.

18. The apparatus of claim 16, wherein the predetermined time interval is selected such that the first signal is measured when the first signal is positive.

19. The apparatus of claim 16, wherein the predetermined time interval is selected such that the second signal is measured substantially when the second signal is approximately zero.

20. The apparatus of claim 15, wherein the exchange group includes at least one contrast agent.

21. The apparatus of claim 15, wherein the exchange group includes at least one paramagnetic contrast agent.

* * * * *

UNITED STATES PATENT AND TRADEMARK OFFICE
CERTIFICATE OF CORRECTION

Page 1 of 1

PATENT NO. : 8,742,755 B2
APPLICATION NO. : 12/936711
DATED : June 3, 2014
INVENTOR(S) : Elena Vinogradov et al.

It is certified that error appears in the above-identified patent and that said Letters Patent is hereby corrected as shown below:

IN THE CLAIMS:

At column 11, claim 1, line 8, please change: "A computer readable medium" to -- A non-transitory computer readable medium --;

At column 11, claim 2, line 36, please change: "The computer readable medium" to -- The non-transitory computer readable medium --;

At column 11, claim 3, line 40, please change: "The computer readable medium" to -- The non-transitory computer readable medium --;

At column 11, claim 4, line 43, please change: "The computer readable medium" to -- The non-transitory computer readable medium --;

At column 11, claim 5, line 46, please change: "The computer readable medium" to -- The non-transitory computer readable medium --;

At column 11, claim 6, line 50, please change: "The computer readable medium" to -- The non-transitory computer readable medium --;

At column 11, claim 7, line 52, please change: "The computer readable medium" to -- The non-transitory computer readable medium --.

Signed and Sealed this
Thirty-first Day of March, 2015

Michelle K. Lee
*Director of the United States Patent and Trademark Office*